(12) United States Patent
Frayne

(10) Patent No.: US 7,125,982 B1
(45) Date of Patent: Oct. 24, 2006

(54) MICROBIAL PRODUCTION OF NUCLEASE RESISTANT DNA, RNA, AND OLIGO MIXTURES

(75) Inventor: Elizabeth Gay Frayne, Diamond Bar, CA (US)

(73) Assignee: Frayne Consultants, Diamond Bar, CA (US)

( * ) Notice: Subject to any disclaimer, the term of this patent is extended or adjusted under 35 U.S.C. 154(b) by 350 days.

(21) Appl. No.: 10/007,489

(22) Filed: Dec. 5, 2001

(51) Int. Cl.
*C07H 21/00* (2006.01)
*C07H 19/00* (2006.01)
*C12N 9/14* (2006.01)

(52) U.S. Cl. ............... 536/25.33; 536/25.32; 536/22.1; 536/25.31; 536/23.1; 536/25.3; 536/26.6; 536/26.71; 536/124; 536/25.34; 435/6; 435/7.92; 435/7.94; 435/71; 435/91; 435/131; 435/154; 435/172

(58) Field of Classification Search ............... 536/22.1, 536/23.1, 25.33, 25.34, 25.36, 25.32, 25.31, 536/25.3, 26.6, 26.71, 124; 435/41, 71, 91, 435/131, 154, 172, 6, 7.92, 7.94

See application file for complete search history.

(56) References Cited

U.S. PATENT DOCUMENTS

| | | | |
|---|---|---|---|
| 5,518,900 A * | 5/1996 | Nikiforov et al. ......... 435/91.1 |
| 5,629,177 A | 5/1997 | Hyman |
| 5,635,488 A | 6/1997 | Cook |
| 5,644,048 A | 7/1997 | Yau |
| 5,650,271 A | 7/1997 | Richards |
| 5,739,311 A | 4/1998 | Lackey et al. |
| 5,883,237 A | 3/1999 | Stec et al. |
| 5,916,777 A | 6/1999 | Kacia et al. |
| 5,932,450 A | 8/1999 | Dattagupta et al. |
| 5,990,300 A | 11/1999 | Hiatt et al. |
| 6,031,092 A | 2/2000 | Just et al. |
| 6,096,880 A | 8/2000 | Kool |
| 6,117,993 A | 9/2000 | Iyer et al. |
| 6,239,265 B1 | 5/2001 | Cook |
| 6,294,664 B1 | 9/2001 | Ravikumar et al. |
| 6,310,198 B1 | 10/2001 | Tang et al. |
| 6,326,478 B1 | 12/2001 | Cheruvallath et al. |

OTHER PUBLICATIONS

Sayers et al. "Phosphorothioate-based site directed mutagenesis for single stranded vectors." Directed Mutagen. 49-69, 1991.*
Sayers et al. Directed Mutagen, 49-69, 1991.*
Melgar, E. and Goldthwait, D. A. "The effects of metals on the mechanism of action of deoxyribonucleaseI" (1968) J. Biol. Chem. 243: p. 4414.
Spitler, S. and Eckstein, F. "Inhibition of deoxyribonucleases by phosphorothioate groups in oligodeoxyribonucleotides" (1988) Nucleic Acids Res 16: pp. 11696-11697 and 11701-11702.
Potter, B.V.L., Romaniuk, P.J., and Eckstein, F. (1983) "The Stereochemical Course of DNA Hydroxysis by SI Nuclease" J. Biol. Chem. 258:1758-1760, p. 1759.

* cited by examiner

*Primary Examiner*—James O. Wilson
*Assistant Examiner*—Devesh Khare

(57) ABSTRACT

The present method describes the use of thio-phosphate as a feed source for micro-organisms and multi-cellular organisms. This compound enters into nucleotide pools and ultimately into polymers of both RNA and DNA forming stable phosphorothioate internucleotide linkages. The method enables the microbial synthesis of both plasmid and phage DNA substituted with phosphorothioate. Furthermore, methods are described for the preparation of phosphorothioate oligo mixtures from recombinant phage DNA grown in modified media for use in antisense studies.

5 Claims, 3 Drawing Sheets

1 2 3 4    5 6 7 8

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
      (A) LENGTH: 22 base pairs
      (B) TYPE: nucleic acid
      (C) STRANDEDNESS: single
      (D) TOPOLOGY: linear

```
        (ii) MOLECULE TYPE: genomic DNA (iii) HYPOTHETICAL: no (iv) ANTI-SENSE: no (vi) ORIGINAL SOURCE:
             (A) ORGANISM: Saccharomyces cerevisiae
             (B) STRAIN: YFL039C genomic clone (x) PUBLICATION INFORMATION:
             (A) AUTHORS:  Murakami Y., Naitou M., Hagiwara H., Shibata T.,
                 Ozawa M., Sasanuma S.I., Sasanuma M., Tsuchiya Y.,
                 Soeda E., Yokoyama K., Yamazaki M., Tashiro H., Eki T.
             (B) TITLE: Analysis of the nucleotide sequence of chromosome
                 VI from Saccharomyces cerevisiae.
             (C) JOURNAL: Nature Genet.
             (D) VOLUME: 10
             (F) PAGES: 261-268
             (G) DATE:1995
             (K) RELEVANT RESIDUES IN SEQ ID NO: 1: 10-31

(xi) SEQUENCE DESCRIPTION: SEQ ID NO: 1:

GAG GTT GCT GCT TTG GTT ATT G                                              22

(2) INFORMATION FOR SEQ ID NO: 2:

(i) SEQUENCE CHARACTERISTICS:
             (A) LENGTH: 22 base pairs
             (B) TYPE: nucleic acid
             (C) STRANDEDNESS: single
             (D) TOPOLOGY: linear (ii) MOLECULE TYPE: genomic DNA (iii) HYPOTHETICAL: no (iv) ANTI-SENSE: yes (vi) ORIGINAL SOURCE:
             (A) ORGANISM: Saccharomyces cerevisiae
             (B) STRAIN: YFL039C genomic clone (x) PUBLICATION INFORMATION:
             (A) AUTHORS:  Murakami Y., Naitou M., Hagiwara H., Shibata T.,
                 Ozawa M., Sasanuma S.I., Sasanuma M., Tsuchiya Y.,
                 Soeda E., Yokoyama K., Yamazaki M., Tashiro H., Eki T.
             (B) TITLE: Analysis of the nucleotide sequence of
                 chromosome VI from Saccharomyces cerevisiae.
             (C) JOURNAL: Nature Genet.
             (D) VOLUME: 10
             (F) PAGES: 261-268
             (G) DATE:1995
             (K) RELEVANT RESIDUES IN SEQ ID NO: 2: 1097-1118

(xi) SEQUENCE DESCRIPTION: SEQ ID NO: 2:

TT GTG GTG AAC GAT AGA TGG AC                                              22
```

MICROBIAL PRODUCTION OF NUCLEASE RESISTANT DNA, RNA, AND OLIGO MIXTURES

BACKGROUND OF THE INVENTION

1. Field of the Invention

The present invention relates to various methods for production of phosphorothioate containing nucleic acids which are generally more nuclease resistant than unsubstituted DNA, RNA, or oligonucleotides. Micro-organisms or cells are used to catalyze the in vivo synthesis of phosphorothioate nucleic acids by incubation in modified media containing thio-phosphate as a source of phosphorus. The method enables the bulk preparation of nuclease resistant double-stranded (ds) DNA, single-stranded (ss) DNA, RNA, or oligo mixtures substituted with phosphorothioate linkages.

Bacteria infected with recombinant phage DNA and grown in thio-phosphate containing media produce single-stranded phage DNA with phosphorothioate linkages. Recombinant phosphorothioate phage DNA can be further processed in vitro to generate oligo mixtures spanning the entire region of a cloned recombinant DNA insert. Such oligo mixtures are not only nuclease resistant but also have enhanced antisense activity by virtue of multiple target sites embodied in an entire recombinant cDNA or exon phage DNA insert. Phosphorothioate containing DNA plasmids or recombinant DNA vectors can also be prepared. The use of thiophosphate in generating phosphorothioate nucleic acids in vivo is not limited by cell type as both prokaryotic and eukaryotic cells incorporate the modified phosphate.

2. Description of Related Disclosures

Phosphorothioate containing analogues of oligonucleotides are widely used for gene ablation, otherwise known as antisense technology, to diminish gene expression in tissue culture cells or in the treatment of entire organ systems as novel pharmaceutical reagents (J. Murray Ed. (1992) "Antisense RNA & DNA," Wiley-Liss, New York; van der Krol, et al (1988) BioTechniques 6:958–975; Clercq, et al (1970) Virology 42:421–428). DNA and RNA oligonucleotides can be chemically synthesized in several hundred milligram to gram quantities (Froehler et al (1986) Nucleic Acids Res. 14:5399–5407; Sinha et al (1983) Tetrahedron Lett. 24:58435846; Letsinger et al (1965) J. American Chem. Soc. 87: 3526; Sinha and Fry (1984) In Sanghui and Cook (Eds) "Carbohydrate Modifications in Antisense Research," American Chemical Society, Washington, D.C.), although they are often used on a smaller scale for research purposes. Phosphorothioate oligos are typically prepared via solid phase synthesis and oxidative sulfurization with the Beaucage or Zon reagent. More recent advances in include the preparation of chirally enriched phosphorothioate oligos (Just et al (2000) U.S. Pat. No. 6,031,092; Stec et al (1999) U.S. Pat. No. 5,883,237) as well as large scale synthesis procedures involving solution phase techniques (Yau (1997) U.S. Pat. No. 5,644,048; Ravikumar et al (1999) U.S. Pat. No. 6,001,982).

Long phosphorothioate polymers (>100 bases) can be generated in vitro using RNA or DNA polymerases and the appropriate phosphorothioate analogues of the nucleoside triphosphates as substrates (Griffiths and Eperon (1987) Nucleic Acids Res. 15:4145–4162; Suh and Eperon (1987) Nucleic Acids Res. (1992) 20:6303–6309; Eckstein (1985) Annu. Rev. Biochem. 54:367–402). Enzymatic synthesis being more costly, is typically used when smaller quantities suffice or longer polymers are required. Enzymatic synthesis results in the stereospecific incorporation of Sp nucleotides with inversion of configuration to the Rp form in the internucleotidic linkage. In this regard, oligodeoxynucleotides of the Rp configuration form a more stable complex with mRNA and hence may be a better ablater of gene expression (Koziolkiewicz et al (1995) Nucleic Acids Res. 23: 5000–5005). Several novel in vitro approaches have been devised for the enzymatic preparation of oligonucleotides involving the formation of concatamers and various means of separating these (Lackey et al (1998) U.S. Pat. No. 5,739,311; Kacian et al (1999) U.S. Pat. No. 5,916,777; Dattagupta et al (1999) U.S. Pat. No. 5,932,450; Kool et al (2000) U.S. Pat. No. 6,096,880).

The utility of antisense oligos for the ablation of gene expression has gained considerable experimental evidence. Typically an antisense oligo hybridizes with its target RNA in a cell and thereby leads to the inactivation of the target transcript. DNA and RNA oligos taken up by cells in culture are rapidly degraded unless they are chemically modified. Phosphorothioate substituted DNA oligos are resistant to nucleases and upon uptake into the cell inhibit gene expression by stimulating an RNase H activity which degrades the RNA component of the mRNA/DNA hybrid formed.

Oligo mixtures have been shown to be more effective in antisense studies than individual oligos (Nieto et al (1994) Science 264:835–839; Morgan et al (1993) Nucleic Acids Res. 21:4615–4620; Dattagupta et al (1998) U.S. Pat. No. 5,739,309) but are not widely used as they are not as readily synthesized. Mixtures of oligos are effective at much lower concentrations and with reduced toxicity. The observations suggest that the rate limiting step for antisense inhibition is the interaction of the oligo with its target mRNA. Mixtures of antisense oligos by sensing a larger mRNA target may be more efficient and thus require lower inhibitory concentrations. An additional advantage of oligo mixtures is reduced toxicity through reduced concentrations and increased specificity. It has been suggested that non-specific effects may result from short stretches of homology between an oligo and another non-target mRNA molecule that may hybridize long enough to be destroyed by RNase H (Wolf (1992) PNAS 89:7305–7309). The use of mixtures of oligos corresponding to different parts of the mRNA to be inactivated should reduce these effects since no one oligo would accumulate to a significant extent leaving the target mRNA as the site of preferred hybridization.

The present invention provides a means for the facile production of phosphorothioate containing oligo mixtures, and DNA or RNA polymers. The method involves the use of bacteria as an economical means to generate milligram quantities of DNase resistant oligo mixtures. Large fermentors could presumably be used to synthesize gram quantities of dsDNA, ssDNA, or oligo mixtures. The nucleic acids generated are stereospecific, corresponding to the preferred more stable Rp configuration for antisense work. To produce antisense oligo mixtures no DNA sequence information is required, simply the orientation of the cloned insert with respect to transcription. For example, cDNA clones that have been inserted unidirectionally into a recombinant vector (Alting-Meese and Short (1989) Nucleic Acids Res. 17:9494–9501) can be manipulated to generate antisense oligos.

SUMMARY OF THE INVENTION

The present invention relies on the in vivo incorporation of thio-phosphate into nucleic acids, introducing nuclease resistant phosphorothioate linkages into both DNA and RNA molecules. Mixtures of oligos spanning a cloned DNA fragment of interest, can be generated by the processing of single-stranded recombinant M13 phage DNAs grown in thio-phosphate containing media. To generate antisense oligo mixtures, the cloned fragment is inserted in the orientation that opposes transcription. M13 recombinant phage substituted with phosphorothioate are purified by standard PEG (polyethyleneglycol) precipitation. The insert is then processed to generate oligonucleotides by enzymatic or physical means. The method can also be used to generate DNase resistant plasmids or recombinant vectors for use in gene therapy or as DNA vaccines. Thiophosphate can be utilized by both prokaryotic and eukaryotic cell types in the synthesis of phosphorothioate substituted nucleic acids.

DESCRIPTION OF THE PREFERRED EMBODIMENTS

Figure 1:
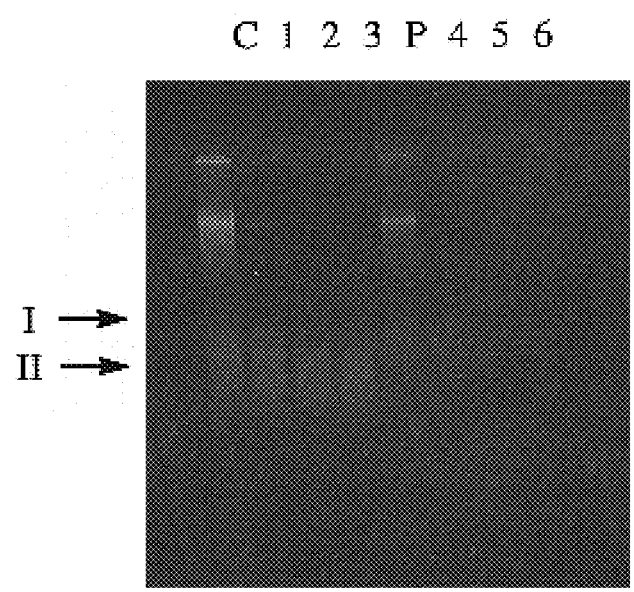
FIG. 1 demonstrates the resistance of M13 phage DNA grown in thio-phosphate media to DNase I digestion. Lanes C and P are control lanes without DNase for normal and thio-phosphate substituted DNA. The two forms of phage DNA indicated by arrows: closed circular (I) and linear (II). Conversion of form I to II during DNase digestion was assayed at 1, 2, and 3 hrs. (lanes 1–3 and 4–5, respectively). By two hrs. (lane 2) form I is completely digested in normal phage DNA samples. In contrast, using DNA from cells grown in thio-phosphate media, no conversion is detected for up to 3 hrs. of incubation (lanes 4–6).

Organisms require a metabolically useful source of phosphorus for DNA replication and continued growth. In many instances inorganic phosphate is used by cells as a source of phosphate in the synthesis of nucleic acids and/or the modification of cellular proteins, etc. The sulfated version of inorganic phosphate or thio-pbosphate is also absorbed and utilized by cells in the synthesis of nucleic acids. The modified phosphate is presumably incorporated into dNTP and NTP precursor pools. Generally to achieve high levels of thio-phosphate incorporation it is necessary to remove all sources of inorganic phosphate from the culture media. For bacterial cells and yeast, minimal medias or chemically defined medias are easily prepared using thio-phosphate instead of phosphate. In other instances it may be useful to deplete nutrient broths of phosphate prior to use. This can be done by magnesium sulfate precipitation in the presence of ammonium hydroxide (Rubin (1973) J. Biol. Chem. 248: 3860). For invertebrate and vertebrate cells the growing use of serum free medias makes it readily possible to substitute thio-phosphate as a source of phosphorus for these cells as well (Jakoby and Pastan, Eds. (1979) In Methods in Enzymology "Cell Culture," Vol. 58; Cell Systems, Inc.).

Bacterial cells respond well to high levels of thio-phosphate producing high yields of recombinant DNA molecules when grown in such medias. The modified phosphate appears to be taken up by cells as readily as inorganic phosphate. The use of a mixture of thio-phosphate and inorganic phosphate results in intermediate levels of thio-phosphate incorporation. It is also possible to first deplete bacterial cells of internal inorganic phosphate by growing the cells in minimal media using glycerol-phosphate as a source of phosphorus. In the absence of organic phosphate a phosphatase is induced which hydrolyzes phosphate esters, such as glycerol phosphate without leading to significant phosphate accumulation.

The preparation of large quantities of thio-phosphate DNA can be readily achieved using bacterial cells and recombinant vectors such as M13. Propagation of M13 bacteriovirus phage in thio-phosphate media results in ssDNA yields similar to phage grown in normal media (5–10 ug/ml of culture). Inserts up to 1 Kb are typically cloned into M13 (Messing (1981) Nucleic Acids Res. 9:309–317). When inserted in the antisense orientation, antisense DNA oligo mixtures can be obtained. It may be of interest to purify recombinant cDNA sequences from vector sequences. There are several ways in which this may be achieved. The most precise method involves the use of restriction enzymes to cleave the recombinant single stranded DNA insert. In this regard, the ability of a particular restriction enzyme to cleave thio-phosphate substituted DNA must be considered. Many enzymes are retarded or blocked by the presence of a phosphorothioate linkage (Taylor et al (1985) Nucleic Acids Res. 14:8749–8764). As a rule four base bair recognition sequence enzymes appear to be less sensitive to the presence of thio-phosphate than six base pair recognition enzymes. Several of the six base pair cutters that are more useful include: Pvu II, Sac I, Sal I, Sma I, Mst II, Hgi AI. Other restriction enzymes that can be used with excess enzyme and prolonged incubation include: Bam HI, Eco RI, Bgl I, and Hind III. Partial cleavage of single-stranded phosphorothioate DNA has also been observed with other enzymes (Lackey et al (1998) U.S. Pat. No. 5,739,311). An alternative approach would be to sonicate or degrade the phage DNA and selectively extract the insert sequences by hybridization with excess minus strand M13 phage DNA attached to magnetic beads or solid phase supports.

After the cDNA insert is purified as required it is necessary to degrade the single-stranded DNA to suitably sized oligos. Many physical methods have been employed to fragment DNA, these include sonication, french press, wharing blender, or hydroshear (Oefner et al (1996) Nucleic Acids Res. 24:3879–3886) (Davis et al (1973) Methods in Enzymology Vol. 21:378–381). It is also possible to degrade thio-phosphate single-stranded DNA with S1 nuclease or DNase I. Normally DNase cleaves double-stranded DNA more readily than single-stranded DNA when magnesium is used in the buffer. However, if the magnesium is replaced with manganese then the efficiency increases (Melgar and Goldthwaite (1968) J. Biol. Chem. 243:4409–4417). The rate of digestion of single-stranded phosphorothioate DNA is still, however, much slower than unsubstituted DNA. DNase I digestion, however, is easy to control by varying the amount of enzyme. With prolonged incubation DNase I will degrade phosphorothioate single-stranded M13 phage DNA into oligos less than 50 bp in length. Previous assays used to measure DNase digestion of phosphorothioate nucleotides were not sensitive enough to detect digestion (Spitzer and Eckstein (1988) Nucleic Acids Res. 16:11691–1170). Furthermore, studies indicating stereoselectivity of S1 for short phosphorothioate nucleotides do not hold for much longer phosphorothioate polymers (Eckstein (1985) Annu. Rev. Biochem. 54:367–402).

Oligo mixtures have been used in antisense studies where the oligos were micro-injected into frog oocytes (Morgan et al (1993) Nucleic Acids Res. 21:4615–4620). Such mixtures were much more effective than any one oligo alone. This can be explained by assuming that the rate limiting step is the intial interaction between the oligo and target mRNA. Presently, oligos are used at concentrations that are in far excess of a one to one ratio of oligo to target even after accounting for the poor uptake of oligos by cells (1–10%). By increasing the mRNA target sites one might expect according to the poisson distribution an exponential increase in effective interactions resulting from the increase in density of target sites. If one assumes a typical mRNA size such as a 1.2 Kb mRNA and an average oligonucleotide size of 30 bp than the number of targets equals N−n+1 where N is 1200 and n is 30. Therefore, a potential decrease in concentration required of at least several orders of magnitude can be expected. Even mixtures of two oligos have been shown to be more effective together at ten fold lower concentrations than either one alone (Nieto et al (1994) Science 264:835–839). However, in general and particularly for cell culture or in vivo studies DNase resistant oligos are required. It is not pratical to synthesize a mixture of 1000 oligos. Therefore, the present method provides a ready means to generate oligo mixtures that are DNase resistant.

Many applications can be envisioned for the use of large gene encoding DNase resistant molecules. Both double-stranded and single-stranded molecules can be produced with thio-phosphate linkages. Such nuclease resistant linkages should help to stablize DNA molecules used in cells or in vivo such as recombinant DNA vaccines (Wolff et al (1990) Science 247:1465–1468) or gene therapy expression constructs. Many bioprocessing and diagnostic procedures involve the contact of cell extracts with purified DNAs. DNase resistant molecules should exhibit greater stability than unmodified molecules with similar specificity. More recently it has been shown that certain CG sequences found in bacteria illicit a strong immune response which is potentiated by phosphorothioate linkages (Weiner et al (1997) PNAS 94:1083310837). Thus bacterial DNAs modified with phosphorothioate backbones have the potential to be strong adjuvants.

EXPERIMENTAL

Example I

Method to Generate Antisense Oligo Mixtures

The propagation of M13 phage in thio-phosphate containing media first requires the cultivation of the appropriate host strain such as JM109 which requires minimal media to select for the F' pillus. Minimal plates are prepared as follows: bactoagar, 10.5 g/L; $K_2HPO_4$ $3H_2O$, 4.5 g/L; $KH_2PO_4$, 4.5 g/L; $(NH_4)_2SO_4$, 1 g/L; sodium citrate $2H_2O$, 0.5 g/L; Adjust pH to 7.4 and autoclave. Then add the following: $MgSO_4.7H_2O$, 0.2 g/L (sterilized separately as a conc. solution); (thiamine HCL, 5 ug/L; glucose, 4 g/L sterilized separately by filtration). Glucose can also be sterilized by autoclaving separately. $FeCl_2$ (500 ug/L) can also be added as needed.

Thio-phosphate containing media is prepared similarly as minimal media except that the inorganic phosphates are replaced with thio-phosphate ($Na_3SPO_3.XH_2O$) 10–15 g/L and KCL (1.5 g/L). Thio-phosphate contains variable amounts of water (10–15 per molecule) not included in molecular weight calculations. It is almost 50% water by weight. Note pH control is important in maximizing thio-phosphate stability. To ensure adequate growth, use a high density innoculum. The preferred pH is neutral or slightly basic. For media to deplete cellular phosphate pools, beta-glycerolphosphate is substituted for inorganic phosphates at a concentration of ~25 g/L.

Several media are required for the production of infectious phage particles: LBM medium (bacto tryptone, 10 g/L; bacto yeast extract, 5 g/L; NaCl, 5 g/L; 2 g/L $MgCl_2.H_2O$; 10 mM Tris/HCL pH 7.5. LBM agar plates (add 15 gm Bacto-agar to 1 liter of LBM medium and autoclave); soft agar (add 7 gm of bacto-agar to 1 liter of LBM medium. Store at 4° C. and heat to 45° C. before use.).

Phage are generated by transforming JM109 cells with the replicative form of M13 DNA or double-stranded DNA using the calcium chloride (Dagert and Ehrlich (1979) Gene 6:23) or DMSO/PEG (Chung et al (1989) PNAS 86:2172–2176). The transformed cells produce infectious particles when grown in nutrient broth. To 0.3 ml of competent cells add 5 ng of DNA and let the mixture sit on ice for 40 min. Then heat shock the cells at 42° C. for 2 min. and add the following: 0.2 ml of fresh JM109 cells and 3 ml of top agar at 45° C. Mix and plate directly onto LBM plates. Let the plates solidify and then incubate at 37° C. until plaques are seen (overnight). The plaques appear as turbid clearings on the bacterial lawn. A plaque can then be picked with a sterile toothpick and used to innoculate 2 ml of LBM broth and grown with shaking overnight. The cells are spun out and the supernatant is saved as phage stock at 4° C. The supernatant (20 ul) can be run directly on a gel to test for the presence of DNA. The titer of the stock should be checked to ensure high yields. The titer should be at least $1 \times 10^{10}$/ml.

To prepare phosphorothioate phage substituted DNA, JM109 cells are incubated overnight in LB broth. The starter culture can be used directly or spun out and washed with thio-phosphate media to remove phosphate present in the yeast extract of LBM broth. Generally 500 ml of thio-phosphate containing media are innoculated with 10–25 ml of overnight culture (high density) and grown for ~1.5 hrs to an OD 600=0.3 (early log phase). At this point infect cells with phage stock at a moi of 1 pfu per 10 bacterial cells. This corresponds to aproximately 500 ul of phage stock. The cells are then incubated at 37° C. with shaking for 3 hr. and not more. For intermediate levels of thio-phosphate, cells are incubated in media containing an equal mixture of thio-phosphate and inorganic phosphate.

M113 phage DNA can be purified by standard PEG precipitation (ppt). Cells are pelleted in a centrifuge at 12,000×g and the supernatant is saved. 125 ml of 2.5 M NaCl, 20% PEG 6000 is added to each 500 ml of phage supernatant. Let sit at room temperature or overnight in the refrigerator. Spin sample for 20 min. at ~12,000×g. Suck off all the supernatant, respin briefly to get drops off the wall of the tube and remove all liquid. Dissolve in TE (10 mm Tris-HCL, pH 8.0, 1 mm EDTA) buffer. Add 2% SDS and heat at 65° C. for 10 min. To remove PEG perform a phenol/chloroform extraction and several chloroform extractions as necessary, until the interface is clear. Ethanol ppt the aqueous layer, pellet and resuspend in sterile water. Traces of genomic DNA and RNA can be removed with DNase (standard magnesium buffer: 50 mM Tris pH 7.5, 1 mM $MgCl_2$, 100 units/ml) and RNase (10 ug/ml) respectively at 24° C. for ~10 min. Chloroform extract and then ethanol ppt. sample.

To process the cloned insert restriction enzymes are used that flank the insert EcoR I and Sal I can be used with mp18 in a suitable buffer (6 mM Tris pH 7.9, 6 mM $MgCl_2$, 150 mM NaCl, 1 mM dithiothreitol). The sample is then run in a non-denaturing agarose gel and the insert excised from the gel. The insert can then be purified by electro-elution.

To fragment the insert DNA the sample is treated with DNase in the presence of manganese (5 mM manganese, 50 mM Tris-HCL, pH 7.5) (Melgar and Goldthwaite (1968) J. Biol. Chem. 243:4409–4417). Use 200–500 units of enzyme per ml and digest overnight at 37° C. The DNase can then be removed by chloroform extraction.

To assay for thio-phosphate incorporation resistance to DNase digestion can be monitored using manganese containing buffer. When the phage DNA sample is run on a high resolving agarose gel the closed circular form is separated from the nicked linear form. The disappearance of the closed circular form can be monitored by incubating an aliquot with 2 units of enzyme in a ten ul reaction for 1–3 hrs. By two hrs, the closed circular form disappears in normal DNA preparations. Modified DNAs are more resistant depending on the ratio of thio-phosphate to phosphate used in the growth medium (FIG. 1). The closed circular form of DNA disappears by 3 hrs. when a 50% ratio of thio-phosphate to phosphate is used compared to the persistance of the circular form when the growth medium contains 100% thio-phosphate. Other traditional methods to examine phosphorothioate nucleotides include $^{31}$P NMR (Eckstein and Jovin (1983) 22:4546–4550).

Example II

In Vivo Synthesis of Phosphorothioate Containing RNA.

Growth of cells in thio-phosphate containing media results in the incorporation of thio-phosphate nucleotides into RNA as well as DNA. The resultant RNAs accumulate and are protected from degradation both in vivo and in vitro during subsequent isolation of total RNA. Both E. coli and yeast are easily grown in minimal medias with thio-phosphate as the only source of phosphorus. S. cerevisiae (Baker's yeast, ATTC #7754) grow in essential minimal media with no phosphates (EMM [Contents/L: 3 g phthalic Acid, K+, 5 g NH$_4$Cl, 20 g dextrose, 1.05 g MgCl$_2$, 6H$_2$O, 14.7 mg CaCl$_2$.2H$_2$O, 1 g KCl, 0.04 g Na$_2$SO$_4$, 1 mg panthothenic acid, 10 mg nicotinic acid, 10 mg myo-inositol, 1 mg biotin, 0.5 mg boric acid, 0.4 mg MnSO$_4$, 0.4 mg ZnSO$_4$.7H$_2$O, 0.2 mg FeCl$_2$.6H$_2$O, 40 ug molybdic, 0.1 mg KI, 40 ug CuSO$_4$.5H$_2$O, 1 mg citric acid], BIO101) and supplemented with thio-phosphate (1–10 g/L) as well as each of the following at 50 mg/L adenine, histidine, leucine, lysine, and uracil (Sp, BIO101). For bacteria see above minmimal media preparation.

Figure 2:
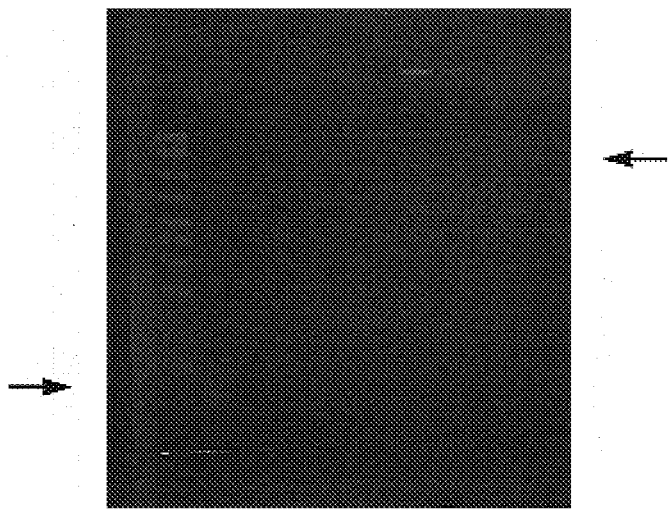
FIG. 2 demonstrates the resistance of *E. coli* RNA from cells grown in thio-phosphate media to RNase digestion. Total RNA was prepared using Quigley and Holmes rapid boiling procedure (see text) to lyse cells and which typically leaves low molecular weight RNA species (lane 1 arrow). The RNA was separated on a non-denaturing agarose gel along with a ds DNA molecular weight marker (50 bp–2 Kb, Bio-Rad). The addition of RNase (⅕, ⅒, ½₀ dilutions of 1 mg/ml; lanes 2–4 respectively) resulted in the disappearance of normal RNA. Lane 5 (arrowhead) shows high molecular weight RNA detected only from cells grown in thio-phosphate media. The RNA is also more resistant to RNase as shown in lanes 6 and 7 using no dilution or a ⅕ dilution of RNase (1 mg/ml).

Normally the Ouigley and Holmes rapid boiling method (Anal. Biochem (1981) 114:193–197) is used to isolate plasmid DNA. RNA from such preparations is generally low molecular weight. When E. coli cells are grown in thio-phosphate media and RNA is prepared using the rapid boiling procedure high molecular weight RNA can be observed. Cells are prepared by diluting an enriched-broth overnight culture one to fifty into minimal media. Grow cells for several hrs. and harvest the same day. For each 1.5 ml of cells centrifuge and resuspended in 200 ul of STET buffer (8% sucrose, 50 mM Tris-base pH 8.0, 50 mM EDTA, 0.1% Trition X-100). Add lysozyme (20 ul of 10 mg/ml solution in Tris pH 8.0) and incubate at room temperature for 5 minutes. Then place in a boiling water bath for 40–50 sec. The sample is spun at 12,000×g for 10 min. The supernatant is then extracted twice to remove proteins such as RNase with StrataClean Resin™. The aqueous phase is then ppt with 1–2 volumes of isopropanol. Ribosomal RNAs are evident as can be judged by running samples on a 1% non-denaturing agarose gel. In contrast, RNA from E. coli grown in normal media is typically found at the bottom of the gel near the bromphenol blue loading dye tracking marker (less than a 50 bp ds DNA marker)(FIG. 2).

Example III

Incorporation of Thio-Phosphate into the DNA of a Complex Organism

Figure 3:
FIG. 3 demonstrates the resistance of intestinal DNA derived from Carassius auratus maintained in an aquarium with thio-phosphate. Lns 1–4 show wild type DNA and Lns 5–8 resistant DNA treated with DNase for 0, 5, 10, and 15 min respectivley.

Thio-phosphate can also be utilized by whole animals and/or complex tissues. Carassius auratus incorporates thio-phosphate into the DNA of intestinal cells; these cells are known to turnover in adults. Fish can be maintained in distilled water with NovAqua and AmQuel conditioners (U.S. Pat. No. 4,666,610). Goldfish flakes are also added for food. Normal phosphate levels in the aquarium are less than 1 mg/L (Hanna Phosphate Test Kit; Hanna Instruments). Fish are transferred to 100 ml of conditioned media with up to 250 mg/L of thio-phosphate added. No adverse reactions are seen in fish incubated for up to two days. Fresh media is prepared daily. Fish are sacrificed and DNA prepared from intestinal cells using DNAzol™ (Molecular Research Center, Ohio). The DNA samples are then tested for resistance to DNase digestion. Samples are incubated in a 50 ul rxn with ~1 ug of DNA and 0.5 units of DNase for 0, 5, 10, 15 min. at room temp. DNA from 250 mg/L thio-phosphate media is much more resistant than wildtype DNA or DNA from 25 mg/L thio-phosphate media. Normal DNA and 25 mg/L thio-phosphate treated DNA is digested after 5 min. while 250 mg/L thio-phosphate treated DNA persists beyond 15 min. of digestion (FIG. 3).

What is claimed is:

1. A method for synthesizing phosphorothioate substituted nucleic acids by
   1) preparing microbial culture media depleted of phosphate
   2) adding thio-phosphate as an alternative source of phosphate to the media
   3) culturing micro-organisms in the modified media containing thiophosphate to allow the uptake and incorporation of thiophosphate into nucleotide precursor pools thereby leading to the synthesis of phosphorothioate internucleotide linkages.

2. The method of claim 1 to generate phosphorothioate recombinant plasmid DNA, recombinant phage DNA including single-stranded M13 phage DNA, or RNA produced from a recombinant viral or plasmid vector by:
   1) transforming bacterial cultures with the desired recombinant DNA plasmid or recombinant DNA phage
   2) growing the transformed cultures in modified media containing thiophosphate as a source of phosphate
   3) isolating the recombinant plasmid DNA, phage DNA, or RNA produced by a recombinant vector from said bacterial cultures.

3. The method of claim 1 to generate partially substituted phosphorothioate recombinant plasmid DNA, recombinant phage DNA, including single-stranded M13 phage DNA, or RNA produced from a recombinant viral or plasmid vector by:
1) transforming bacterial cultures with the desired recombinant DNA plasmid or recombinant DNA phage
2) growing the transformed cultures in modified media containing a mixture of thiophosphate and unmodified phosphate as a source of phosphate
3) isolating the recombinant plasmid DNA, phage DNA, or RNA produced by a recombinant vector from said bacterial cultures.

4. The method of claim 1 wherein the cells cultured in thio-phosphate media or induced to uptake thio-phosphate are of eukaryotic origin.

5. The method of claim 1 wherein the alternative source of phosphate is a derivative of thiophosphate including but not limited to dithiophosphate and/or methylthiophosphate.

* * * * *